(12) United States Patent
Arlt et al.

(10) Patent No.: US 6,258,813 B1
(45) Date of Patent: Jul. 10, 2001

(54) D4 RECEPTOR SELECTIVITY PIPERAZINE DERIVATIVES

(75) Inventors: Michael Arlt, Seeheim-Jugenheim; Henning Bottcher, Darmstadt; Gerd Bartoszyk, Weiterstadt; Christoph Seyfried, Seeheim-Jugenheim, all of (DE)

(73) Assignee: Merck Patent Gesellschaft mit (DE)

( * ) Notice: Subject to any disclaimer, the term of this patent is extended or adjusted under 35 U.S.C. 154(b) by 0 days.

(21) Appl. No.: 09/254,489

(22) PCT Filed: Sep. 3, 1997

(86) PCT No.: PCT/EP97/04789
§ 371 Date: Mar. 9, 1999
§ 102(e) Date: Mar. 9, 1999

(87) PCT Pub. No.: WO98/11068
PCT Pub. Date: Mar. 19, 1998

(30) Foreign Application Priority Data
Sep. 13, 1996 (DE) ................................ 196 37 237

(51) Int. Cl.[7] ............ A61K 31/496; A61K 31/506; C07D 401/06; C07D 401/14; C07D 409/14

(52) U.S. Cl. ............ 514/252.11; 514/252.18; 514/252.14; 514/253.01; 514/253.11; 514/255.03; 514/252.13; 544/295; 544/357; 544/360; 544/364; 544/392

(58) Field of Search ............ 544/295, 360, 544/364, 392, 357, 379; 514/252, 255, 252.18, 252.14, 253.11, 253.01, 252.13, 255.03, 252.11

(56) References Cited

U.S. PATENT DOCUMENTS

| | | | |
|---|---|---|---|
| 4,959,368 | * 9/1990 | Awaya et al. | 514/252 |
| 5,432,177 | 7/1995 | Baker et al. | 514/253 |
| 5,538,965 | 7/1996 | Tehim et al. | 514/211 |
| 5,594,141 | * 1/1997 | Yuan et al. | 544/295 |
| 5,681,956 | 10/1997 | Thurkauf et al. | 544/295 |
| 5,684,020 | 11/1997 | Peglion et al. | 514/320 |
| 5,731,438 | * 3/1998 | Cook et al. | 544/368 |

FOREIGN PATENT DOCUMENTS

| | | |
|---|---|---|
| 745598 | 12/1996 | (EP) . |
| 9420497 | 9/1994 | (WO) . |
| 9421630 | 9/1994 | (WO) . |
| 9422839 | 10/1994 | (WO) . |
| 9517400 | 6/1995 | (WO) . |
| 9616040 | 5/1996 | (WO) . |

OTHER PUBLICATIONS

Vantol et al, Nature, vol. 350, p. 610–614, 1991.*
Saxena, Pharmac. Ther. vol. 66, p. 339–368, 1995.*
Adachi et al, Chemical Abstracts, vol. 131, No. 58848, Abstract for WO99/31062 (Jun. 24, 1999).*
WO9422839–English Abstract, (Oct. 13, 1994).
WO9421630–English Abstract, (Sep. 29, 1994).

* cited by examiner

Primary Examiner—Emily Bernhardt
(74) Attorney, Agent, or Firm—Millen, White, Zelano & Branigan, P.C.

(57) ABSTRACT

Piperazine derivatives of the formula I

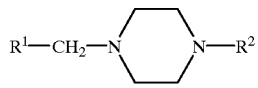

in which $R^1$ and $R^2$ have the meanings given in claim 1 are dopamine ligands with a selectivity for the D4 receptor and are suitable for the treatment and prophylaxis of states of anxiety, depression, schizophrenia, obsessions, Parkinson's disease, tardive dyskinesia, nausea and disorders of the gastro-intestinal tract.

21 Claims, No Drawings

D4 RECEPTOR SELECTIVITY PIPERAZINE DERIVATIVES

The invention relates to piperazine derivatives of the formula I

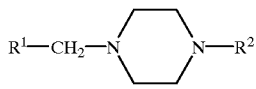

in which
R¹ is pyridyl or phenyl, each of which is monosubstituted by Ph or by 2- or 3-thienyl,
R² is Ph' or Het,
Ph and Ph' in each case independently of one another are phenyl, it being possible for both radicals to be in each case unsubstituted or mono-, di- or trisubstituted by F, Cl, Br, I, OH, OA, A, CF₃, NO₂, CN, COA, CONH₂, CONHA, CONA₂ or 2- or 3-thienyl,
Het is a saturated, partially or fully unsaturated mono- or bicyclic heterocyclic radical having 5 to 10 ring members, it being possible for 1 or 2 N and/or 1 or 2 O atoms to be present and it being possible for the heterocyclic radical to be mono- or disubstituted by F, Cl, Br, I, OA, CF₃, A or NO₂, and
A is alkyl having 1 to 6 C atoms,
and to the physiologically acceptable salts thereof.

The invention was based on the object of finding novel compounds which can be used for the preparation of pharmaceuticals.

It has been found that the compounds of the formula I and their physiologically acceptable acid addition salts have valuable pharmacological properties. The compounds of the formula I are dopamine ligands with a selectivity for the D4 receptor, in comparison with D2 and D3 receptors (method analogous to Creese et al., European J. Pharmacol. 46, 377–381 (1977); with ³H-spiroperidol as ligand for dopamine receptors and cloned, human dopamine D4, D3 and D2 receptors (available from: Receptor Biology Inc., Baltimore Md. 21227, USA). The compounds are suitable for the treatment of schizophrenia, cognitive deficiencies, anxiety, depressions, nausea, tardive dyskinesia, disturbances of the gastro-intestinal tract, or Parkinson's disease. They have effects on the central nervous system, mainly additional 5-HT$_{1A}$-agonistic and 5-HT reuptake-inhibitory effects. Furthermore, the compounds have serotonin-agonistic and -antagonistic properties. They inhibit the binding of tritiated serotonin ligands to hippocampus receptors (Cossery et al., European J. Pharmacol. 140 (1987), 143–155). Changes in DOPA accumulation in the striatum and changes in 5-HTP accumulation in the nuclei raphes are observed as well (Seyfried et al., European J. Pharmacol. 160 (1989), 31–41). Moreover, analgetic and antihypertensive effects are observed; thus, in catheterized conscious spontaneously hypertonic rats (strain SHR/Okamoto/NIH-MO-CHB-Kisslegg; Methods, cf. Weeks and Jones, Proc. Soc. Exptl. Biol. Med. 104 (1960), 646–648), the directly measured blood pressure is lowered after administering the compounds orally. They are also suitable for prophylaxis and for controlling the sequelae of cerebral infarctions (apoplexia cerebri), such as apoplexy and cerebral ischaemias.

Compounds of the formula I and their physiologically acceptable acid addition salts can therefore be used as pharmaceutically active ingredients for anxiolytics, antidepressants, antipsychotics, neuroleptics and/or antihypertonics, and also as intermediates for the preparation of other pharmaceutically active ingredients.

The invention relates to piperazine derivatives of the formula I and to their physiologically acceptable acid addition salts.

The radical A is alkyl having 1, 2, 3, 4, 5 or 6, in particular 1 or 2, C atoms, preferably methyl, furthermore also ethyl, n-propyl, isopropyl, n-butyl, sec-butyl or tert-butyl. OA is preferably methoxy, furthermore also ethoxy, n-propoxy, isopropoxy, n-butoxy, isobutoxy, sec-butoxy or tert-butoxy. NHA is preferably methylamino, furthermore ethylamino, isopropylamino, n-butylamino, isobutylamino, sec-butylamino or tert-butylamino. NA₂ is preferably dimethylamino, furthermore N-ethyl-N-methylamino, diethylamino, di-n-propylamino, diisopropylamino or di-n-butylamino. As a result, CO-NHA is preferably N-methylcarbamoyl or N-ethylcarbamoyl; CO—NA₂ is preferably N,N-dimethylcarbamoyl or N,N-diethylcarbamoyl.

The radical R¹ is preferably phenyl which is unsubstituted or monosubstituted by 3-thienyl, biphenyl which is unsubstituted or monosubstituted by OA, CN, CF₃, F, Br or Cl, or 2-, 3- or 4-pyridyl which can be especially preferably substituted by 3-thienyl, phenyl or p-, m- or o-F-phenyl. If R¹ is substituted or unsubstituted pyridyl, then the 3-pyridyl radical is preferred.

The radical R² is preferably phenyl which is unsubstituted or mono-, di- or trisubstituted by F, Cl, Br, OH, OA, A, CONH₂, COA, CF₃, CN and/or NO₂, or Het which is substituted analogously, it being possible for Het to be preferably 1,4-benzodioxane, 2-, 3- or 4-pyridyl, 2-, 4-, 5- or 6-pyrimidinyl, 3- or 4-pyridazinyl, 2- or 3-pyrazinyl.

The rule that all radicals such as, for example, Ph which can occur more than once in a molecule can be identical or different applies to the entire invention.

Accordingly, the invention particularly relates to those compounds of the formula I in which at least one of the abovementioned radials has one of the meanings given above as being preferred. Some preferred groups of compounds can be expressed by the formulae Ia to Ik below, which correspond to the formula I and in which the radicals which are not detailed further have the meanings given in the formula I, but in which, in Ia, R¹ is 3-pyridyl which is substituted in the 5-position;
in Ib, R is 2-pyrimidinyl;
in Ic, R¹ is phenyl and R² is pyridyl or pyrimidinyl, each of which is unsubstituted or monsubstituted;
in Id, R¹ is biphenyl and R² is unsubstituted or mono-, di- or trisubstituted phenyl;
in Ie, R¹ is biphenyl and R² is unsubstituted or monosubstituted 1,4-benzodioxanyl, benzofuranyl, pyridyl, pyrazinyl, pyridazinyl or pyrimidinyl;
in If, R¹ has a meaning given in Ia or Ib and R² is mono-, di- or trisubstituted phenyl;
in Ig, R¹ has a meaning given in Ia or Ib and R² is monosubstituted or unsubstituted pyridyl, pyrimidinyl, pyrazinyl or pyridazinyl;
in Ih, R² is 2-pyrimidinyl and R¹ is meta-susbtituted phenyl or is pyrid-3-yl which is substituted in the 5-position;
in Ii, R² is 2-pyrimidinyl and R¹ is substituted phenyl or substituted pyrid-3-yl, the substituents preferably being OCH₃, F or 2- or 3-thienyl;
in Ik, R¹ has a meaning given in Ia and the substituent is phenyl or o- or p-fluorophenyl.

The invention furthermore relates to a process for the preparation of piperazine derivatives of the formula I and of salts thereof, characterized in that a compound of the formula II

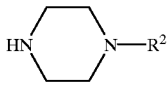

in which $R^2$ has the abovementioned meaning is reacted with a compound of the formula III $$R^1-CH_2-L \qquad III$$

in which
L is Cl, Br, I, OH, O—CO—A, O—CO—Ph, O—SO$_2$—Ar, Ar representing phenyl or tolyl and A representing alkyl, or another OH group which is reactively esterified, or a leaving group which is readily nucleophilically substitutable, and
$R^1$ has the abovementioned meaning,
or in that a compound of the formula IV $$H_2N-R^2 \qquad IV$$

in which
$R^2$ has the abovementioned meaning
is reacted with a compound of the formula V

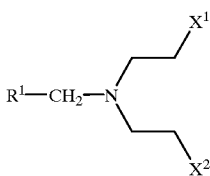

in which
$X^1$ and $X^2$ can be identical or different and are Cl, Br, I, OH or a reactive, functionally modified OH group and $R^1$ has the abovementioned meaning,
or in that a compound of the formula VI

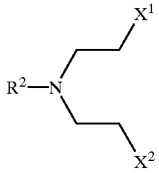

in which
$R^2$, $X^1$ and $X^2$ have the meanings which have already been given
is reacted with a compound of the formula VII $$R^1-CH_2-NH_2 \qquad VII$$

in which
$R^1$ has the abovementioned meaning,
or in that a compound which otherwise corresponds to the formula I but which contains one or more reducible group(s) and/or one or more additional C—C and/or C—N bond(s) instead of one or more hydrogen atom is treated with a reducing agent,
or in that a compound which otherwise corresponds to the formula I but which contains one or more solvolysable group(s) instead of one or more hydrogen atom is treated with a solvolysing agent,
and/or in that, if appropriate, a radical $R^1$ and/or $R^2$ is converted into another radical $R^1$ and/or $R^2$, for example by cleaving an OA group with the formation of an OH group and/or derivatizing a CN, COOH or COOA group and/or, for example, in that a primary or secondary N atom is alkylated and/or a resulting base or acid of the formula I is converted into a salt thereof by treating it with an acid or base.

Besides, the compounds of the formula I are prepared by methods known per se as they are described in the literature (for example in standard publications such as Houben-Weyl, Methoden der Organischen Chemie [Methods in organic chemistry], Georg Thieme Verlag, Stuttgart; Organic Reactions, John Wiley & Sons, Inc., New York; DE-A 41 01 686), under reaction conditions as they are known and suitable for the abovementioned reactions. It is also possible to utilize variants which are known per se and not described in greater detail in the present text.

If desired, the starting materials for the claimed process can also be formed in situ in such a way that they are not isolated from the reaction mixture but immediately reacted further to give the compounds of the formula I.

As a rule, the compounds of the formulae II and III are known; those compounds of the formulae II and III which are not known are readily obtainable in analogy to the known compounds.

Most of the piperazine derivatives of the formula II are known and can be prepared, for example, by reacting bis(2-chloroethyl)amine or the corresponding ammonium chloride with aniline derivatives, aminonaphthalene derivatives or aminobiphenyl derivatives of the formula Ph'—NH$_2$ or with amino-substituted heterocyclic compounds of the formula Het—NH$_2$.

As a rule, the pyridines, benzyl compounds, naphthalene derivatives or biphenyl derivatives of the formula III are known and in most cases they are commercially available. Furthermore, the compounds can be prepared from known compounds by electrophilic or, in specific cases, also nucleophilic aromatic substitution. However, compounds of the formula III can be prepared in particular by introducing a radical L into compounds of the formula R'—CH$_3$, for example by radical substitution, or by converting an existing radical L in a compound of the formula III into a different radical L. Thus, for example, an OH group can be esterified or subjected to nucleophilic substitution with halogen.

The reaction of the compounds II and III proceeds by methods as they are known from the literature for the alkylation of amines. In the absence of a solvent, the components may be melted together, if appropriate in a sealed tube or in an autoclave. However, it is also possible to react the compounds in the presence of an inert solvent. Examples of suitable solvents are hydrocarbons, such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile, if appropriate also mixtures of these solvents with each other, or mixtures with water. Addition of an acid-binding agent, for example of an alkali metal hydroxide, alkali metal carbonate, alkali metal bicarbonate, alkaline earth metal hydroxide, alkaline earth metal carbonate or alkaline earth metal bicarbonate, or of another salt of a weak acid of the alkali metal or akaline earth metal, preferably of potassium, sodium or calcium, or addition of an organic base such as triethylamine, dimethylaniline, pyridine or quinoline, or of an excess of piperazine derivative of the formula II may be advantageous. Depending on the prevailing conditions, the reaction time is between a few minutes and 14 days, and the reaction temperature is between approximately 0 and 150°, normally between 20 and 130°.

Moreover, compounds of the formula I can be prepared by reacting amines of the formula IV with the compounds of the formula V.

As a rule, the amines of the formula IV are known. They can furthermore be prepared for example by reducing suitable nitro compounds, it being possible for the nitro compounds to be prepared by nitration on the aromatic ring, as is generally known.

Compounds of the formula V can be prepared, for example, by reducing diesters of the formula alkylOOC—$CH_2$—N($CH_2R^1$)—$CH_2$—COOalkyl to give compounds of the formula HO—$CH_2$—$CH_2$—N($CH_2R^1$) —$CH_2$—$CH_2OH$, followed, if appropriate, by reaction with $SOCl_2$ or $PBr_3$.

Compounds of the formula V can also be prepared by reacting secondary amines of the formula HN($CH_2$—$CH_2X^1$) ($CH_2$—$CH_2$—$X^2$) with halides of the formula $R^1$—$CH_2$—Hal(Hal=Cl, Br).

To prepare compounds of the formula I, it is furthermore also possible to react compounds of the formula VI with amines of the formula VII. The compounds of the formula VI resemble the compounds of the formula V structurally and can be prepared analogously. The same applies to the compounds of the formula VII with regard to the amines of the formula V. In addition, the amines of the formula VII can be prepared by processes for the synthesis of primary amines which are known per se, for example Gabriel synthesis.

The reaction of the compounds IV and V, or VI, with VII proceeds by methods as they are known from the literature for the alkylation of amines and which are already indicated above.

It is furthermore possible to obtain a compound of the formula I by treating a precursor which, instead of hydrogen atoms, contains one or more reducible group(s) and/or one or more additional C—C and/or C—N bond(s) with a reducing agent, preferably at temperaures between −80 and +250° in the presence of at least one inert solvent.

Reducible groups (groups which can be replaced by hydrogen) are, in particular, oxygen in a carbonyl group, hydroxyl, arylsulfonyloxy (for example p-toluenesulfonyloxy), N-benzenesulfonyl, N-benzyl or O-benzyl.

In principle, it is possible to convert compounds which only contain one, or those which contain two or more of the abovementioned groups, or additional bonds, adjacent to each other by means of reduction to give a compound of the formula I; substituents in the group I which the starting compound contains can be reduced at the same time. To this end, it is preferred to use nascent hydrogen or complex metal hydrides, furthermore Wolff-Kishner reduction, and reductions using hydrogen gas with transition metal catalysis.

If nascent hydrogen is used as reducing agent, it may be produced for example by treating metals with weak acids or with bases. Thus, for example, a mixture of zinc and alkali metal hydroxide solution or of iron and acetic acid may be used. Also suitable is the use of sodium or another alkali metal, dissolved in an alcohol such as ethanol, isopropanol, butanol, amyl alcohol or isoamyl alcohol or phenol. An aluminium nickel alloy in alkaline-aqueous solution, if appropriate with addition of ethanol, may furthermore be used. Also suitable for producing nascent hydrogen are sodium amalgam or aluminium amalgam in aqueous-alcoholic or aqueous solution. The reaction can also be carried out in heterogenous phase, it being expedient to use an aqueous and a benzene or toluene phase.

Reducing agents which are furthermore employed particularly advantageously are complex metal hydrides such as $LiAlH_4$, $NaBH_4$, diisobutylaluminium hydride or $NaAl(OCH_2CH_2OCH_3)_2H_2$ and diborane, if desired with addition of catalysts such as $BF_3$, $AlCl_3$ or LiBr. Solvents which are particularly suitable for this purpose are ethers such as diethyl ether, di-n-butyl ether, THF, dioxane, diglyme or 1,2-dimethoxyethane, and also hydrocarbons such as benzene. Solvents which are suitable for the reduction with $NaBH_4$ are mainly alcohols such as methanol or ethanol, furthermore water, and aqueous alcohols. When carrying out these methods, the reduction is preferably carried out at temperatures between −80 and +150°, in particular between approximately 0 and approximately 100°.

—CO groups in acid amides can be reduced especially advantageously to $CH_2$ groups by using $LiAlH_4$ in THF at temperatures between approximately 0 and 66°.

It is furthermore possible to reduce one or more carbonyl groups to $CH_2$ groups using the method of Wolff-Kishner, for example by treatment with anhydrous hydrazine in absolute ethanol under pressure at temperatures between approximately 150 and 250°. Sodium alkoxide is advantageously used as the catalyst. The reduction may also be varied by the method of Huang-Minlon by carrying out the reaction with hydrazine hydrate in a solvent which is miscible with water and which has a high boiling point, such as diethylene glycol or triethylene glycol, in the presence of alkali, such as sodium hydroxide. As a rule, the reaction mixture is boiled for about 3–4 hours.

The water is subsequently distilled off and the hydrazone formed is decomposed at temperatures of up to about 200°. The Wolff-Kishner reduction may also be carried out in dimethyl sulfoxide at room temperature, using hydrazone.

In addition, it is possible to carry out certain reductions by using $H_2$ gas with the catalytic effect of transition metals, for example Raney Ni or Pd. In this manner, for example Cl, Br, I, SH or else, in some cases, OH groups, may be replaced by hydrogen. Equally, nitro groups may be converted into $NH_2$ groups by catalytic hydrogenation using $Pd/H_2$ in methanol.

Compounds which otherwise correspond to the formula I but which contain one or more solvolysable group(s) instead of one or more H atoms can be solvolysed, in particular hydrolysed, to give the compounds of the formula I.

The starting materials for solvolysis can be obtained for example by reacting compounds of the formula II which correspond to the formula III but which contain one or more solvolysable group(s) instead of one or more H atoms.

Furthermore, a compound of the formula I may be converted into a different compound of the formula I by methods known per se.

Compounds of the formula I in which $R^1$ is a radical substituted by $CONH_2$, $CONHA$ or $CONA_2$ can be obtained by derivatizing suitable substituted compounds of the formula I by means of partial hydrolysis. It is furthermore possible first to hydrolyse cyano-substituted compounds of the formula I to give acids and to amidate the acids with primary or secondary amines. Preferred is the reaction of the free carboxylic acid with the amine under peptide synthesis conditions. This reaction is preferably carried out in the presence of a dehydrating agent, for example a carbodiimide such as dicycolhexylcarbodiimide or N-(3-dimethylaminopropyl)-N-ethylcarbodiimide, furthermore propanephosphonic anhydride (cf. Angew. Chem. 92, 129 (1980)), diphenylphosphorylazide or 2-ethoxy-N-ethoxy-carbonyl-1,2-dihydroquinoline, in an inert solvent, for example a halogenated hydrocarbon such as dichloromethane, an ether such as THF or dioxane, an amide such as DMF or dimethylacetamide, a nitrile such as acetonitrile, at temperatures between approximately −10 and 40°, preferably between 0 and 30°.

Alternatively, it is especially advantageous to prepare the nitriles the other way around by eliminating water starting from the amides, for example by means of trichloroacetyl chloride/$Et_3N$ [Synthesis (2), 184 (1985)] or with $POCl_3$ (J. Org. Chem. 26, 1003 (1961)).

The resulting base of the formula I can be converted into the corresponding acid addition salt by using an acid. Acids which are suitable for this reaction are those which yield physiologically acceptable salts. Thus, inorganic acids may be used, for example sulfuric acid, hydrohalic acids such as hydrochloric acid or hydrobromic acid, phosphorus acids such as orthophosphoric acid, nitric acid, sulfamic acid, furthermore organic acids, viz. aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid; benzenesulfonic acid, p-toluenesulfonic acid, napthalenemono- and -disulfonic acids, laurylsulfuric acid.

If desired, the free bases of the formula I can be set free from their salts by treatment with strong bases such as sodium hydroxide, potassium hydroxide, sodium carbonate or potassium carbonate, unless other acidic groups are present in the molecule. In those cases where the compounds of the formula I have free acid groups, salt formation can also be achieved by treatment with bases. Suitable bases are alkali metal hydroxides, alkaline earth metal hydroxides or organic bases in the form of primary, secondary or tertiary amines.

The invention furthermore relates to the use of the compounds of the formula I and of their physiologically acceptable salts for the preparation of pharmaceutical products, in particular via a non-chemical route. They can be brought into a suitable pharmaceutical form together with at least one excipient or auxiliary and, if appropriate, in combination with one or more other active ingredient(s).

The invention furthermore relates to compositions, in particular to pharmaceutical products, comprising at least one compound of the formula I and/or a physiologically acceptable salt thereof. These products can be employed as pharmaceuticals in human and veterinary medicine. Suitable excipients are organic or inorganic substances which are suitable for enteral (for example oral), parenteral or topical administration and which do not react with the novel compounds, for example water, vegetable oils, benzyl alcohols, polyethylene glycols, gelatin, carbohydrates such as lactose or starch, magnesium stearate, talc or petroleum jelly. Pharmaceutical forms which are used for enteral administration are, in particular, tablets, including coated tablets, capsules, syrups, liquids, drops or suppositories, pharmaceutical forms which are used for parenteral administration are solutions, preferably oily or aqueous solutions, furthermore suspensions, emulsions or implants, and pharmaceutical forms which are used for topical administration are ointments, creams or powders. The novel compounds can also be lyophilized and the resulting lyophilizates used for example for the preparation of injectable products.

The above products can be sterilized and/or comprise auxiliaries such as glidants, preservatives, stabilizers and/or wetting agents, emulsifiers, salts for modifying the osmotic pressure, buffer substances, colours, flavourings and/or perfumes. If desired, they can additionally comprise one or more other active ingredients, for example one or more vitamins.

The compounds of the formula I and their physiologically acceptable salts can be used in therapeutic treatment of the human or animal body and for combating diseases. They are suitable for the treatment of diseases of the central nervous system, such as nervous tension, depression, states of anxiety, schizophrenia, disorders of the gastrointestinal tract, nausea, tardive dyskinesia, Parkinson's disease and/or psychoses, and side-effects after treatment of hypertension (for example with α-methyldopa). The compounds can furthermore be used in endocrinology and gynaecology, for example for the therapy of acromegalism, hypogonadism, secondary amenorrhoea, premenstrual syndrome, undesired puerperal lactation, furthermore for the prophylaxis and therapy of cerebral disorders (for example migraine), in particular in geriatrics similarly to certain ergot alkaloids and for combating the sequelae of cerebral infarctions (apoplexia cerebri), such as apoplexy and cerebral ischaemias.

As a rule, the substances according to the invention are administered analogously to commercially available products (for example bromocriptin, dihydro-ergocornin), preferably in doses between approximately 0.2 and 500 mg, in particular between 0.2 and 50 mg per unit dose. The daily dose is preferably between approximately 0.001 and 10 mg/kg body weight. The lower doses are between approximately 0.2 and 500 mg, in particular between 0.2 and 50 mg, per unit dose. The daily dose is preferably between approximately 0.001 and 10 mg/kg body weight. The lower doses (approximately 0.2 to 1 mg per unit dose; approximately 0.001 to 0.005 mg/kg body weight) are particularly suitable for the use as a medicament for migraine; doses between 10 and 50 mg per unit dose are preferred for the remaining indications. The specific dose for every individual patient, however, depends on a wide range of factors, for example on the efficacy of the specific compound employed, on the age, the body weight, the general health, the gender, the diet, the timing and route of administration, the rate of excretion, the combination of pharmaceutically active ingredients and the severity of the disease in question for which the therapy is intended. Oral administration is preferred.

In the examples which follow, "customary work-up" means: if required, water is added, the mixture is extracted with dichloromethane, the phases are separated, the organic phase is dried over sodium sulfate, filtered and evaporated, and the product is purified by chromatography on silica gel and/or by crystallization. Temperatures are indicated in °C. Rf values were obtained by thin-layer chromatography on silica gel. $M^++1$ values were determined by FAB-MS (fast atom bombardment mass spectroscopy).

EXAMPLE 1

2.04 g of 3-chloromethyl-5-phenylpyridine ("A") [obtainable for example by radical chlorination of 3-methyl-5-phenylpyridine] and 1.62 g of 1-phenylpiperazine are dissolved in 200 ml of acetonitrile and the mixture is stirred for six hours at room temperature. After customary work-up, 1-phenyl-4-[(5-phenyl-3-pyridyl)methyl]piperazine, m.p. 83–85°, is obtained.

The following are obtained analogously by reacting "A":
with
1-(2-fluorophenyl)piperazine,
1-(2-fluorophenyl)-4-[(5-phenyl-3-pyridyl)methyl]piperazine, trihydrochloride, m.p. 217–219°;
with
1-(2-methoxyphenyl)piperazine,
1-(2-methoxyphenyl)-4-[(5-phenyl-3-pyridyl)methyl]piperazine trihydrochloride dihydrate, m.p. 235–236°;
with
1-(2-pyridyl)piperazine,
1-(2-pyridyl)-4-[(5-phenyl-3-pyridyl)methyl]piperazine, m.p. 103–105°;
with
1-(3-trifluoromethylphenyl)piperazine,
1-(3-trifluoromethylphenyl)-4-[(5-phenyl-3-pyridyl)methyl]piperazine trihydrochloride, m.p. 216–219°.

The following are obtained analogously by reacting 2-chloromethyl-4-phenylpyridine:
with
1-phenylpiperazine,
1-phenyl-4-[(4-phenyl-2-pyridyl)methyl]piperazine;
with
1-(2-fluorophenyl)piperazine,
1-(2-fluorophenyl)-4-[(4-phenyl-2-pyridyl)methyl]piperazine;
with
1-(2-methoxyphenyl)piperazine,
1-(2-methoxyphenyl)-4-[(4-phenyl-2-pyridyl)methyl]piperazine;
with
1-(2-pyridyl)piperazine,
1-(2-pyridyl)-4-[(4-phenyl-2-pyridyl)methyl]piperazine;
with
1-(3-trifluoromethylphenyl)piperazine,
1-(3-trifluoromethylphenyl)-4-[(4-phenyl-2-pyridyl)methyl]piperazine;
with
1-(2-pyrimidinyl)piperazine,
1-(2-pyrimidinyl)-4-[(4-phenyl-2-pyridyl)methyl]piperazine.

The following are obtained analogously by reacting 2-chloromethyl-4-(4-fluorophenyl)pyridine:
with
1-phenylpiperazine,
1-phenyl-4-[(4-(4-fluorophenyl)-2-pyridyl)methyl]piperazine;
with
1-(2-fluorophenyl)piperazine,
1-(2-fluorophenyl)-4-[(4-(4-fluorophenyl)-2-pyridyl)methyl]piperazine;
with
1-(2-methoxyphenyl)piperazine,
1-(2-methoxyphenyl)-4-[(4-(4-fluorophenyl)-2-pyridyl)methyl]piperazine;
with
1-(2-pyridyl)piperazine,
1-(2-pyridyl)-4-[(4-(4-fluorophenyl)-2-pyridyl)methyl]piperazine;
with
1-(3-trifluoromethylphenyl)piperazine,
1-(3-trifluoromethylphenyl)-4-[(4-(4-fluorophenyl)-2-pyridyl)methyl]piperazine;
with
1-(2-pyrimidinyl)piperazine, 1-(2-pyrimidinyl)-4-[(4-(4-fluorophenyl)-2-pyridyl)methyl]piperazine trihydrochloride dihydrate, m.p. 193–195°;
with
1-(5-fluoropyrimidin-2-yl)piperazine,
1-(5-fluoropyrimidin-2-yl)-4-[(4-(4-fluorophenyl)-2-pyridyl)methyl]piperazine.

EXAMPLE 2

Starting from 1.10 g of 3-chloromethyl-5-(4-fluorophenyl)pyridine ("B") [obtainable, for example, by radical chlorination of 3-methyl-5-(4-fluorophenyl)-pyridine], reaction with 0.82 g of 1-(2-pyrimidinyl)piperazine in 200 ml of acetonitrile at room temperature analogously to Example 1 gives 1-(2-pyrimidinyl)-4-[(5-(4-fluorophenyl)-3-pyridyl)methyl]piperazine, m.p. 97–98°, after customary work-up.

The following are obtained analogously by reacting "B":
with
1-(1,4-benzodioxan-6-yl)piperazine,
1-(1,4-benzodioxan-6-yl)-4-[(5-(4-fluorophenyl)-3-pyridyl)methyl]piperazine trihydrochloride, m.p. 256–259°;
with
1-(4-nitrophenyl)piperazine,
1-(4-nitrophenyl)-4-[(5-(4-fluorophenyl)-3-pyridyl)methyl]piperazine dihydrochloride, m.p. 264°;
with
1-(3,5-dichloro-4-methoxyphenyl)piperazine,
1-(3,5-dichloro-4-methoxyphenyl)-4-[(5-(4-fluorophenyl)-3-pyridyl)methyl]piperazine dihydrochloride, m.p. 163°;
with
1-(4-methoxyphenyl)piperazine,
1-(4-methoxyphenyl)-4-[(5-(4-fluorophenyl)-3-pyridyl)methyl]piperazine trihydrochloride, m.p. 211°;
with
1-(3,4-dimethoxyphenyl)piperazine,
1-(3,4-dimethoxyphenyl)-4-[(5-(4-fluorophenyl)-3-pyridyl)methyl]piperazine trihydrochloride, m.p. 244°
with
1-(2-fluorophenyl)piperazine,
1-(2-fluorophenyl)-4-[(5-(4-fluorophenyl)-3-pyridyl)methyl]piperazine dihydrochloride, m.p. 210°;
with
1-(3,5-dimethyl-4-methoxyphenyl)piperazine,
1-(3,5-dimethyl-4-methoxyphenyl)-4-[(5-(4-fluorophenyl)-3-pyridyl)methyl]piperazine trihydrochloride, m.p. 251°;
with
1-(2-nitrophenyl)piperazine,
1-(2-nitrophenyl)-4-[(5-(4-fluorophenyl)-3-pyridyl)methyl]piperazine dihydrochloride, m.p. 247 ;
with
1-(3-chloro-5-trifluoromethylpyrid-2-yl)piperazine,
1-(3-chloro-5-trifluoromethylpyrid-2-yl)-4-[(5-(4-fluorophenyl) -3-pyridyl)methyl]piperazine dihydrochloride, m.p. 153°;
with
1-(3-methoxyphenyl)piperazine,
1-(3-methoxyphenyl)-4-[(5-(4-fluorophenyl)-3-pyridyl)methyl]piperazine trihydrochloride, m.p. 232°;

with 1-(2-hydroxyphenyl)piperazine, 1-(2-hydroxyphenyl)-4-[(5-(4-fluorophenyl)-3-pyridyl)methyl]piperazine dihydrochloride, m.p. 239°;

with 1-(2-pyrazinyl)piperazine, 1-(2-pyrazinyl)-4-[(5-(4-fluorophenyl)-3-pyridyl)methyl]piperazine dihydrochloride hydrate, m.p. 140°;

with 1-(4-fluorophenyl)piperazine, 1-(4-fluorophenyl)-4-[(5-(4-fluorophenyl)-3-pyridyl)methyl]piperazine dihydrochloride, m.p. 181°;

with 1-(3-trifluoromethyl-4-chlorophenyl)piperazine, 1-(3-trifluoromethyl-4-chlorophenyl)-4-[(5-(4-fluorophenyl)-3-pyridyl)methyl]piperazine sesquihydrochloride, m.p. 230°;

with 1-(2-methylphenyl)piperazine, 1-(2-methylphenyl)-4-[(5-(4-fluorophenyl)-3-pyridyl)methyl]piperazine dihydrochloride, m.p. 258°;

with 1-(4-chlorophenyl)piperazine, 1-(4-chlorophenyl)-4-[(5-(4-fluorophenyl)-3-pyridyl)methyl]piperazine dihydrochloride hydrate, m.p. 135°;

with 1-(2-pyridyl)piperazine, 1-(2-pyridyl)-4-[(5-(4-fluorophenyl)-3-pyridyl)methyl]piperazine trihydrochloride dihydrate, m.p. 203°;

with 1-(2-pyrimidinyl)piperazine, 1-(2-pyrimidinyl)-4-[(5-(4-fluorophenyl)-3-pyridyl)methyl]piperazine maleate, m.p. 172°;

with 1-(3-trifluoromethylphenyl)piperazine, 1-(3-trifluoromethylphenyl)-4-[(5-(4-fluorophenyl)-3-pyridyl)methyl]piperazine sesquihydrochloride, m.p. 237°;

with 1-(4-methylcarbonylphenyl)piperazine, 1-(4-methylcarbonylphenyl)-4-[(5-(4-fluorophenyl)-3-pyridyl)methyl]piperazine sesquihydrochloride, m.p. 211°;

with 1-phenylpiperazine, 1-phenyl-4-[(5-(4-fluorophenyl)-3-pyridyl)methyl]piperazine dihydrochloride hydrate, m.p. 207°.

EXAMPLE 3

Starting from 3-biphenylylmethyl chloride ("C") [obtainable, for example, by radical substitution of 3-methylbiphenyl], reaction with 1-(2-methoxyphenyl)piperazine analogously to Example 1 gives 1-(2-methoxyphenyl)-4-(3-biphenylylmethyl)piperazine maleate, m.p. 158–160°;

The following are obtained analogously by reacting "C":

with 1-phenylpiperazine, 1-phenyl-4-(3-biphenylylmethyl)piperazine maleate, m.p. 181–1830°;

with 1-(4-cyanophenyl)piperazine, 1-(4-cyanophenyl)-4-(3-biphenylylmethyl)piperazine, m.p. 139°;

with 1-(2-methoxy-5-aminocarbonylphenyl)piperazine, 1-(2-methoxy-5-aminocarbonylphenyl)-4-(3-biphenylylmethyl)piperazine dihydrochloride, m.p. 193–196°;

with 1-(2-methoxy-5-cyanophenyl)piperazine, 1-(2-methoxy-5-cyanophenyl)-4-(3-biphenylylmethyl)piperazine hydrochloride, m.p. 227–229°.

EXAMPLE 4

A stirred suspension of 200 mg of NaOH (solid) in 22 ml of diethylene glycol dimethyl ether is treated, at a temperature of 100°, with 1.0 g of 2-[4-(3-bromobenzyl)piperazino]pyrimidine, 0.72 g of 4-trifluoromethylbenzeneboronic acid, 56 mg of tetrakis-triphenylphosphinepalladium, suspended in 10 ml of diethylene glycol dimethyl ether. Then, the mixture is heated at 150° and stirred for a further 1.5 hours. After cooling, the reaction mixture is treated with 50 ml of half-concentrated aqueous HCl solution and extracted twice using in each case 10 ml of dichloromethane, the extract is dried over $Na_2SO_4$ and the solvent is removed. The residue is taken up in a small amount of ether and chromatographed over silica gel using ether/petroleum ether in a ratio of 3:2. This gives 1-(2-pyrimidinyl)-4-(4'-trifluoromethyl-3-biphenylylmethyl)piperazine as an oil, $R_f$=0.44 (ether/petroleum ether 3:2). Treatment with ethereal HCl solution gives the hydrochloride of 1-(2-pyrimidinyl)-4-(4'-trifluoromethyl-3-biphenylylmethyl)piperazine.

EXAMPLE 5

5.2 ml of n-butyllithium, corresponding to 8.3 mmol, are added dropwise to a solution of 0.75 ml of 3-bromothiophene in 1 ml of ether at −78° and the mixture is stirred for 15 minutes. 1.8 g of $ZnBr_2$, suspended in 3 ml of THF/ether (1:1), are subsequently added and the mixture is allowed to come to room temperature. The mixture is stirred for 30 minutes until two phases are formed, cooled again and treated with 11.2 mg of $PdCl_2$ (dppf) . The mixture is stirred for approximately 12 hours, during which process the temperature is allowed to climb to room temperature. For work-up, the mixture is acidified with 1-molar HCl solution and extracted twice using in each case 30 ml of ethyl acetate, the organic phase is dried over $Na_2SO_4$ and the solvent is removed. The residue is taken up in a small amount of ether and chromatographed over silica gel with ether/petroleum ether in a ratio of 1:1. This gives 1-(2-pyrimidinyl)-4-(3-(3-thienyl)benzyl)piperazine as an oily residue. Treatment with ethereal maleic acid solution gives the maleate of 1-(2-pyrimidinyl)-4-(3-(3-thienyl)benzyl)piperazine, m.p. 208°.

EXAMPLE 6

Starting from 4'-trifluoromethyl-3-biphenylylmethyl chloride ("G") [obtainable for example, by radical substitution of 4'-trifluoromethyl-4-methylbiphenyl], reaction with 1-(2-methoxyphenyl)piperazine analogously to Example 3 gives 1-(2-methoxyphenyl)-4-(4'-trifluoromethyl-3-biphenylylmethyl)piperazine.

The following are obtained analogously by reaction of "G":

with 1-phenylpiperazine, 1-phenyl-4-(4'-trifluoromethyl-3-biphenylylmethyl)piperazine;

with 1-(2-aminocarbonylbenzofuran-5-yl)piperazine,
1-(2-aminocarbonylbenzofuran-5-yl)-4-(4'-trifluoromethyl-3-biphenylylmethyl)piperazine;

with 1-(4-trifluoromethylphenyl)piperazine,
1-(4-trifluoromethylphenyl)-4-(4'-trifluoromethyl-3-biphenylylmethyl)piperazine;

with 1-(2-methoxy-5-aminocarbonylphenyl)piperazine,
1-(2-methoxy-5-aminocarbonylphenyl)-4-(4'-trifluoromethyl-3-biphenylylmethyl)piperazine;

with 1-(2-methoxy-5-trifluoromethylphenyl)piperazine
1-(2-methoxy-5-trifluoromethylphenyl)-4-(4'-trifluoromethyl-3-biphenylylmethyl)piperazine.

EXAMPLE 7

A solution of 1.6 g of 1-pyrimidin-2-ylpiperazine in 200 ml of THF is treated with 2.75 g of 3-chloromethyl-4'-trifluoromethylbiphenyl ("H") [obtainable, for example, by radical chlorination of 3-methyl-4'-trifluoromethylbiphenyl], dissolved in 30 ml of THF, and the mixture is stirred for 4 hours at room temperature. After customary work-up, 1-pyrimidin-2-yl-4-[(4'-trifluoromethyl-3-biphenylyl)methyl]piperazine is obtained.

The following are obtained analogously by reaction of "H":

with 3-chloromethyl-4'-methoxybiphenyl,
1-pyrimidin-2-yl-4-[(4'-methoxy-3-biphenylyl)methyl]piperazine dihydrochloride, m.p. 227°;

with 3-chloromethyl-2'-fluorobiphenyl,
1-pyrimidin-2-yl-4-[(2'-fluoro-3-biphenylyl)methyl]piperazine maleate, m.p. 157°;

with 3-chloromethyl-3'-methoxybiphenyl,
1-pyrimidin-2-yl-4-[(3'-methoxy-3-biphenylyl)methyl]piperazine maleate, m.p. 170°;

with 3-chloromethyl-2'-methoxybiphenyl,
1-pyrimidin-2-yl-4-[(2'-methoxy-3-biphenylyl)methyl]piperazine maleate, m.p. 145°;

with 3-chloromethyl-3'-fluorobiphenyl,
1-pyrimidin-2-yl-4-[(3'-fluoro-3-biphenylyl)methyl]piperazine maleate, m.p. 183°;

with 3-chloromethyl-4'-fluorobiphenyl,
1-pyrimidin-2-yl-4-[(4'-fluoro-3-biphenylyl)methyl]piperazine maleate, m.p. 198°;

with 3-(2-thienyl)benzyl chloride,
1-pyrimidin-2-yl-4-[3-(2-thienyl)benzyl]piperazine maleate, m.p. 181°;

with 3-(3-thienyl)benzyl chloride,
1-pyrimidin-2-yl-4-[3-(3-thienyl)benzyl]piperazine maleate, m.p. 208°;

with 4-(2-thienyl)benzyl chloride,
1-pyrimidin-2-yl-4-[4-(2-thienyl)benzyl]piperazine;

with 4-(3-thienyl)benzyl chloride,
1-pyrimidin-2-yl-4-[4-(3-thienyl)benzyl]piperazine;

with 2-(2-thienyl)benzyl chloride,
1-pyrimidin-2-yl-4-[2-(2-thienyl)benzyl]piperazine;

with 2-(3-thienyl)benzyl chloride,
1-pyrimidin-2-yl-4-[2-(3-thienyl)benzyl]piperazine;

with 3-(2-thienyl)-5-chloromethylpyridine,
1-pyrimidin-2-yl-4-[3-(2-thienyl)pyrid-5-ylmethyl]piperazine;

with 3-(3-thienyl)-5-chloromethylpyridine,
1-pyrimidin-2-yl-4-[3-(3-thienyl)pyrid-5-ylmethyl]piperazine

EXAMPLE 8

A mixture of 0.6 g of 1-(2-methoxyphenyl)-4-[(5-phenyl-3-pyridyl)methyl]piperazine [obtainable as described for Example 1], 1.8 g of pyridine hydrochloride and 50 ml of pyridine is boiled for 3 hours. The mixture is cooled and evaporated, and work-up is as usual, yielding 1-(2-hydroxyphenyl)-4-[(5-phenyl-3-pyridyl)methyl]piperazine.

The following are obtained analogously by ether cleavage:

from 1-(2-methoxyphenyl)-4-[(4-phenyl-2-pyridyl)methyl]piperazine,
1-(2-hydroxyphenyl)-4-[(4-phenyl-2-pyridyl)methyl]piperazine;

from 1-(2-methoxyphenyl)-4-[(4-(4-fluorophenyl)-2-pyridyl)methyl]piperazine,
1-(2-hydroxyohenyl)-4-[(4-(4-fluorophenyl)-2pyridyl)methyl]piperazine;

from 1-(3,5-dichloro-4-methoxyphenyl)-4-[(5-(4-fluorophenyl)-3-pyridyl)methyl]piperazine,
1-(3,5-dichloro-4-hydroxyphenyl)-4-[(5-(4-fluorophenyl)-3-pyridyl)methyl]piperazine;

from 1-(4-methoxyphenyl)-4-[(5-(4-fluorophenyl)-3-pyridyl)methyl]piperazine,
1-(4-hydroxyphenyl)-4-[(5-(4-fluorophenyl)-3-pyridyl)methyl]piperazine;

from 1-(3,4-dimethoxyphenyl)-4-[(5-(4-fluorophenyl)-3-pyridyl)methyl]piperazine,
1-(3,4-dihydroxyphenyl)-4-[(5-(4-fluorophenyl)-3-pyridyl)methyl]piperazine;

from 1-(3,5-dimethyl-4-methoxyphenyl)-4-[(5-(4-fluorophenyl)-3-pyridyl)methyl]piperazine,
1-(3,5-dimethyl-4-hydroxyphenyl)-4-[(5-(4-fluorophenyl)-3-pyridyl)methyl]piperazine;

from 1-(3-methoxyphenyl)-4-[(5-(4-fluorophenyl)-3-pyridyl)methyl]piperazine,
1-(3-hydroxyphenyl)-4-[(5-(4-fluorophenyl)-3-pyridyl)methyl]piperazine;

from
- 1-(2-methoxyphenyl)-4-(3-biphenylylmethyl)piperazine,
- 1-(2-hydroxyphenyl)-4-(3-biphenylylmethyl)piperazine;

from
- 1-(2-methoxy-5-aminocarbonylphenyl)-4-(3-biphenylmethyl)piperazine,
- 1-(2-hydroxy-5-aminocarbonylphenyl)-4-(3-biphenylylmethyl)piperazine;

from
- 1-(2-methoxy-5-cyanophenyl)-4-(3-biphenylylmethyl)piperazine,
- 1-(2-hydroxy-5-cyanophenyl)-4-(3-biphenylylmethyl)piperazine;

from
- 1-(2-methoxy-5-aminocarbonylphenyl)-4-(2'-cyano-4-biphenylylmethyl)piperazine,
- 1-(2-hydroxy-5-aminocarbonylphenyl)-4-(2'-cyano-4-biphenylylmethyl)piperazine;

from
- 1-(2-methoxy-5-cyanophenyl)-4-(2'-cyano-4-biphenylylmethyl)piperazine,
- 1-(2-hydroxy-5-cyanophenyl)-4-(2'-cyano-4-biphenylylmethyl)piperazine.

EXAMPLE 9

A mixture of 130 mg of 1-(3-biphenylyl)piperazine, 53 mg of 3-bromoanisole, 57 mg of sodium tert-butyl alkoxide and 8 mg of $[PdCl_2\{P(o-tolyl)_3\}_2]$ in 10 ml of toluene is heated for 3 hours at 100°. After the reaction mixture has cooled to room temperature, it is taken up in 40 ml of ether and washed with saturated NaCl solution. The organic phase is separated off and dried over $Na_2SO_4$ and the solvent is removed. The residue is taken up in a small amount of ether and chromatographed over silica gel. This gives 1-(3-methoxyphenyl)-4-(3-biphenylyl)piperazine as an oily residue, FAB-MS: $M^++1:359$.

The examples which follow relate to pharmaceutical products:

Example A
Vials

A solution of 100 g of an active ingredient of the formula I and 5 g of disodium hydrogen phosphate in 3 l of twice-distilled water is brought to pH 6.5 with 2 N hydrochloric acid, sterile-filtered, dispensed into vials, lyophilized and sealed under sterile conditions. Each vial comprising 5 mg of active ingredient.

Example B
Suppositories

A mixture of 20 mg of an active ingredient of the formula I is melted with 100 g of soya lecithin and 1400 g of cocoa butter, and the mixture is poured into moulds and allowed to cool. Each suppository comprises 20 mg of active ingredient.

Example C
Solution

A solution is prepared from 1 g of an active ingredient of the formula I, 938 g of $NaH_2PO_4 \times 2\ H_2O$, 28.48 g of $Na_2HPO_4 \times 12\ H_2O$ and 0.1 g of benzalkonium chloride in 940 ml of twice-distilled water. The mixture is brought to pH 6.8, made up to 1 l and sterilized by irradiation. This solution can be used in the form of eyedrops.

Example D
Ointment 500 mg of an active ingredient of the formula I are mixed with 99.5 g of petroleum jelly under aseptic conditions.

Example E
Tablets

A mixture of 1 kg of active ingredient of the formula I, 4 kg of lactose, 1.2 kg of potato starch, 0.2 kg of talc and 0.1 kg of magnesium stearate is tabletted in a customary manner in such a way that each tablet comprises 10 mg of active ingredient.

Example F
Coated tablets

The mixture of Example E is tabletted and the tablets are subsequently coated in a customary manner with sucrose, potato starch, talc, tragacanth and colorant.

Example G
Capsules 2 kg of active ingredient of the formula I are filled into hard gelatin capsules in a customary manner such that each capsule comprises 20 mg of the active ingredient.

Example H
Ampoules

A solution of 1 kg of active ingredient of the formula I in 60 l of twice-distilled water is dispensed into ampoules, lyophilized under aseptic conditions and sealed under sterile conditions. Each ampoule comprises 10 mg of active ingredient.

What is claimed is:

1. A piperazine derivative of formula I

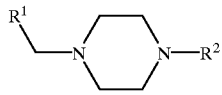

I wherein
   $R^1$ is 5-(4-fluorophenyl)-3-pyridyl, 5-phenyl-3-pyridyl, 5-(3-thienyl)-3-pyridyl, 3-(2-fluorophenyl)-phenyl, 3-(3-methoxyphenyl)-phenyl, 3-(2-thienyl)-phenyl, or 3-(3-thienyl)-phenyl;
   $R^2$ is 2-pyrimidyl, 2-pyridyl, 3,5-dichloro-4-methoxyphenyl, 2-nitrophenyl, 2-chloro-4-trifluoromethyl-phenyl, 2-pyrazinyl, 4-fluorophenyl or 4-chlorophenyl;
or a physiologically acceptable salt thereof.

2. The piperazine derivative according to claim 1, which is:
   1-(2-pyrimidinyl)-4-(3-(3-thienyl]benzyl)-piperazine;
   1-[5-(4-fluorophenyl)pyrid-3-ylmethyl]-4-(2-pyrimidyl) piperazine;
   1-(4-chlorophenyl)-4-[5-(4-fluorophenyl)-3-pyridylmethyl)piperazine; or
   2-[4-(5-(3-thienyl)-3-pyridylmethyl)-1-piperazinyl] pyrimidine.

3. The piperazine derivative according to claim 1, wherein $R^1$ is phenyl monosubstituted by 3-thienyl.

4. The piperazine derivative according to claim 1, wherein $R^1$ is substituted 3-pyridyl.

5. The piperazine derivative according to claim 1, wherein $R^1$ is 3-pyridyl substituted in the 5-position.

6. The piperazine derivative according to claim 1, wherein $R^2$ is 2-pyrimidinyl.

7. The piperazine derivative according to claim 1, wherein $R^1$ is 3-pyridyl substituted in the 5-position and $R^2$ is mono- di- or trisubstituted phenyl.

8. The piperazine derivative according to claim 1, wherein $R^1$ is 3-pyridyl substituted in the 5-position and $R^2$ is monosubstituted or unsubstituted pyridyl, pyrimidinyl, or pyrazinyl.

9. The piperazine derivative according to claim 1, wherein $R^2$ is 2-pyrimidinyl and $R^1$ is meta-substituted phenyl or pyrid-3-yl substituted in the 5-position.

10. The piperazine derivative according to claim 1, wherein $R^2$ is 2-pyrimidinyl and $R^1$ is substituted phenyl or substituted pyrid-3-yl, wherein the substituent is 3-thienyl.

11. The piperazine derivative according to claim 1, wherein $R^1$ is 3-pyridyl substituted in the 5-position by phenyl or o- or p-fluorophenyl.

12. The piperazine derivative according to claim 1, wherein the piperazine derivative or the physiologically acceptable salt thereof is:

1-(2-pyridyl-4-[(5-phenyl-3-pyridyl)methyl]-piperazine);

1-(3,5-dichloro-4-methoxyphenyl)-4-[5-(4-fluorophenyl)-3-pyridyl)methyl]piperazine dihydrochloride;

1-(2-nitrophenyl)-4-[(5-(4-fluorophenyl)-3-pyridyl)methyl]piperazine dihydrochloride;

1-(4-fluorophenyl)-4-[(5-(4-fluorophenyl)-3-pyridyl)methyl]piperazine dihydrochloride;

1-(4-chlorophenyl)-4-[(5-(4-fluorophenyl)-3-pyridyl)methyl]piperazine dihydrochloride hydrate;

1-(2-pyridyl)-4-[(5-(4-fluorophenyl)-3-pyridyl)methyl] piperazine trihydrochloride dihydrate;

1-(2-pyrimidinyl)-4-[5-(4-fluorophenyl-3-pyridyl) methyl]piperazine maleate;

1-(2-pyrimidinyl)-4-(3-(3-thienyl)benzyl)piperazine;

1-pyrimidin-2-yl-4-[3-(2-thienyl)benzyl]piperazine maleate; or 1-pyrimidin-2-yl-4-[3-(3-thienyl)benzyl]piperazine maleate.

13. A piperazine derivative of formula I

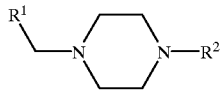

I wherein
$R^1$ is 5-(4-fluorophenyl)-3-pyridyl, 5-phenyl-3-pyridyl, 5-(3-thienyl)-3-pyridyl, 3-(2-fluorophenyl)-phenyl, 3-(3-methoxyphenyl)-phenyl or 3-(3-thienyl)-phenyl;
$R^2$ is 2-pyrimidyl, 2-pyridyl, 3,5-dichloro-4-methoxyphenyl, 2-nitrophenyl, 2-chloro-4-trifluoromethyl-phenyl, 2-pyrazinyl, 4-fluorophenyl or 4-chlorophenyl;
or a physiologically acceptable salt thereof.

14. A process for the preparation of a piperazine derivative of formula I according to claim 1, and of salts thereof, wherein a compound of the formula II

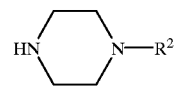

II in which $R^2$ as defined below is reacted with a compound of the formula III

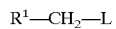

III wherein
L is Cl, Br, I, OH, O—CO—A, O—CO—Ph, O—SO$_2$—Ar, Ar representing phenyl or tolyl and A representing alkyl, or another OH group which is reactively esterified, or a leaving group which is readily nucleophilically substitutable,
$R^1$ is as defined below, or a compound of the formula IV

IV wherein $R^2$ as defined below is reacted with a compound of the formula V

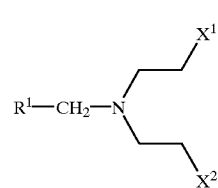

V wherein $X^1$ and $X^2$ can be identical or different and are Cl, Br, I, OH or a reactive, functionally modified OH group and $R^1$ as defined below,
or a compound of the formula VI

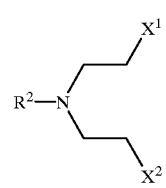

VI wherein $R^2$, as defined below and $X^1$ and $X^2$ and defined above is reacted with a compound of the formula VII

VII wherein $R^1$ is defined below,
whereby a piperazine derivative is made having formula I:

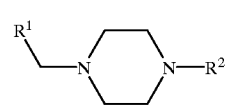

I wherein
$R^1$ is 5-(4-fluorophenyl)-3-pyridyl, 5-phenyl-3-pyridyl, 5-(3-thienyl)-3-pyridyl, 3-(2-fluorophenyl)-phenyl, 3-(3-methoxyphenyl)-phenyl, 3-(2-thienyl)-phenyl or 3-(3-thienyl)-phenyl, R² is 2-pyrimidyl, 2-pyridyl, 3,5-dichloro-4-methoxyphenyl, 2-nitrophenyl, 2-chloro-4-trifluoromethyl-phenyl, 2-pyrazinyl, 4-fluorophenyl or 4-chlorophenyl;

and the physiologically acceptable salts thereof.

15. A process for the preparation of a pharmaceutical product, comprising bringing the derivative and/or the physiologically acceptable salt thereof according to claim 1 into a suitable pharmaceutical form together with at least one solid, liquid or semiliquid excipient or auxiliary.

16. A pharmaceutical composition comprising an effective amount of a compound of claim 1, and a physiologically acceptable salt carrier.

17. A process for preparing a pharmaceutical by incorporating an effective amount of a compound according to claim 1.

18. A method for treating anxiety in a patient in need thereof, comprising administering to the patient an effective amount of a compound of claim 1.

19. A method for treating schizophrenia in a patient in need thereof, comprising administering to the patient an effective amount of a compound of claim 1.

20. A method for treating depression in a patient in need thereof, comprising administering to the patient an effective amount of a compound of claim 1.

21. A method for treating Parkinson' disease in a patient in need thereof, comprising administering to the patient an effective amount of a compound of claim 1.

* * * * *

UNITED STATES PATENT AND TRADEMARK OFFICE
CERTIFICATE OF CORRECTION

PATENT NO. : 6,258,813 B1 Page 1 of 1
APPLICATION NO. : 09/254489
DATED : July 10, 2001
INVENTOR(S) : Michael Arlt It is certified that error appears in the above-identified patent and that said Letters Patent is hereby corrected as shown below:

Column 17, line 41 reads "malcate", should read --maleate--

Signed and Sealed this

Fourth Day of November, 2008

JON W. DUDAS
*Director of the United States Patent and Trademark Office*